United States Patent
Iwamoto

(10) Patent No.: US 9,151,727 B2
(45) Date of Patent: Oct. 6, 2015

(54) LIQUID MEMBRANE TYPE ION-SELECTIVE ELECTRODE

(71) Applicant: HORIBA, Ltd., Kyoto-shi, Kyoto (JP)

(72) Inventor: Yasukazu Iwamoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 13/727,356

(22) Filed: Dec. 26, 2012

(65) Prior Publication Data

US 2013/0168246 A1 Jul. 4, 2013

(30) Foreign Application Priority Data

Dec. 28, 2011 (JP) ................................. 2011-287801

(51) Int. Cl.
*G01N 27/333* (2006.01)

(52) U.S. Cl.
CPC .................................... *G01N 27/333* (2013.01)

(58) Field of Classification Search
CPC ............... G01N 27/302; G01N 27/36; G01N 27/333–27/401; G01N 27/414–27/4148; C03C 4/18
USPC ................. 204/400, 414, 415, 416–419, 433; 205/775, 787.5, 789
See application file for complete search history.

(56) References Cited

U.S. PATENT DOCUMENTS

| | | | |
|---|---|---|---|
| 5,656,241 A * | 8/1997 | Seifert et al. | 422/82.06 |
| 6,200,444 B1 * | 3/2001 | Ahlers et al. | 204/418 |
| 2002/0134679 A1 * | 9/2002 | Terashima et al. | 204/435 |

FOREIGN PATENT DOCUMENTS

| | | |
|---|---|---|
| EP | 0450473 A2 | 10/1991 |
| EP | 0450474 A1 | 10/1991 |
| JP | 6396456 U | 6/1988 |
| JP | 63138255 | 6/1988 |
| JP | 03127252 U | 12/1991 |
| JP | 10197474 A | 7/1998 |
| JP | 2002514540 A | 5/2002 |
| JP | 2005308720 | 11/2005 |
| JP | 2007033333 | 2/2007 |

OTHER PUBLICATIONS

Parthasarathy, N. et al., "Supported Liquid Membrane for Analytical Separation of Transition Metal Ions. Part I. Complexation properties of 1,10-didecyl-1, 10-diaza-18-crown-6", Analytica Chimica Acta, vol. 254, Issues 1-2, pp. 1-7, Nov. 1991, 7 pages.
European Patent Office, Extended European Search Report of EP12198195-5, Mar. 27, 2013, Germany, 5 pages.
Japanese Patent Office, Office Action Issued in Japanese Patent Application No. 2011-287801, Jan. 22, 2015, 2 pages.

* cited by examiner

*Primary Examiner* — Gurpreet Kaur
(74) *Attorney, Agent, or Firm* — Alleman Hall McCoy Russell & Tuttle LLP

(57) ABSTRACT

This invention relates to a liquid membrane type ion-selective electrode that can restrain an electric potential fluctuation of an inner electrode due to ultraviolet rays and that can conduct an analysis with high accuracy. The liquid membrane type ion-selective electrode comprises a liquid membrane type ion-sensitive membrane wherein a predetermined ionophore is supported by a base material, an inner electrode that has electrical conductivity and that is arranged at a position on the ion-sensitive membrane through which light transmitted is incident, an internal solution that contains an electrolyte and that makes contact with the ion-sensitive membrane and the inner electrode, wherein the ion-sensitive membrane contains an ultraviolet absorber or an ultraviolet reflecting agent having an insulative property.

4 Claims, 3 Drawing Sheets

LIQUID MEMBRANE TYPE ION-SELECTIVE ELECTRODE

FIELD OF THE ART

This invention relates to a liquid membrane type ion-selective electrode comprising an ion-sensitive membrane of a liquid membrane type wherein an ionophore is supported.

BACKGROUND ART

A variety of ionophores (ion-selective ligands) that can selectively capture a specific ion are conventionally known. Furthermore, a liquid membrane type ion-selective electrode comprising a liquid membrane type ion-sensitive membrane wherein an ionophore is supported has been developed by making use of the ionophores (patent document 1). It is possible for this liquid membrane type ion-selective electrode to detect a variety of analyte ions by changing the ionophore according to the target ion.

PRIOR ART DOCUMENT

Patent Document

Patent document 1 Japanese Unexamined Patent Application Publication No. 2007-33333
Patent document 2 Japanese Unexamined Patent Application Publication No. 63-138255
Patent document 3 Japanese Unexamined Patent Application Publication No. 2005-308720

DISCLOSURE OF THE INVENTION

Problems to be Solved by the Invention

For example, a resin such as polyvinyl chloride and transparent silicone rubber is generally used as a base material of the ion-sensitive membrane of this liquid membrane type ion-selective electrode. However, generally the resin is high in ultraviolet ray transmission as compared with glass. Accordingly, if a flat type analyzer as described in the patent document 2 comprising a liquid membrane type ion-selective electrode is used, an inner electrode is positioned just below the ion-sensitive membrane so that the ultraviolet rays passing through the ion-sensitive membrane are irradiated on the inner electrode. As a result, an electrical voltage fluctuation problem occurs, causing sensor deterioration.

Conventionally, in order to prevent deterioration of the sensor due to the ultraviolet rays, a means such as using a package provided with a light blocking cover is provided until just prior to the sensor being used (patent document 3).

However, even though the cover is provided, it is necessary to open the package cover while conducting the analysis, and thus it is not possible to prevent the electrical voltage fluctuation of the inner electrode due to the ultraviolet rays at the time of analysis.

Accordingly, the present claimed invention intends to provide a liquid membrane type ion-selective electrode that can restrain the electronic voltage fluctuation of the inner electrode due to ultraviolet rays, and that can conduct the analysis with high accuracy.

Means to Solve the Problems

Conventionally, it has been found that performance of the ion-sensitive membrane is affected if an ion-sensitive membrane contains an ultraviolet absorber or an ultraviolet reflecting agent. However, after keen examination by the present inventors, it has been revealed that the electrical voltage fluctuation of the internal electrode due to the ultraviolet rays can be restrained while keeping the performance of the ion-sensitive membrane even though the ion-sensitive membrane contains an ultraviolet absorber or the ultraviolet reflecting agent so long as the ultraviolet absorber of the ultraviolet reflecting agent has insulative properties.

More specifically, the liquid membrane type ion-selective electrode comprises a liquid membrane type ion-sensitive membrane wherein a predetermined ionophore (ion-selective ligand) is supported by a base material, an electrically conductive inner electrode that is arranged at a position at which the ion-sensitive membrane transmitted light is incident, and an internal solution that contains an electrolyte and that makes contact with the ion-sensitive membrane and the inner electrode, and is characterized by the ion-sensitive membrane containing an ultraviolet absorber or an ultraviolet reflecting agent having an insulative property.

In accordance with this arrangement, since the liquid membrane type ion-sensitive member is mixed with the ultraviolet absorber or the ultraviolet reflecting agent having the insulative property, it is possible to prevent the inner electrode from being irradiated by the ultraviolet rays even though a flat type analysis device is constituted by the use of the liquid membrane type ion-selective electrode. As a result, it becomes possible to restrain the electric potential fluctuation of the inner electrode due to the ultraviolet rays so that a highly accurate analysis can be conducted.

The base material of the ion-sensitive membrane is not especially limited, and for example, a transparent resin having high ultraviolet ray permeability such as polyvinyl chloride, transparent silicone rubber, polyethylene, polypropylene, polyvinyl alcohol is used as the base material of the ion-sensitive membrane. In the case where the base material of the ion-sensitive membrane is a resin having high ultraviolet ray permeability, this invention performs effectively. In addition, if the resin is used as the base material, it is possible to use a simple method for making a membrane, whereby a resin, an ionophore and a ultraviolet absorber or a ultraviolet reflecting agent are dissolved into a solvent and the dissolved resin, ionophore and ultraviolet ray absorber or ultraviolet reflecting agent are applied to a response part and then the solvent is evaporated. As a result, the ion-sensitive membrane can be made with ease.

The inner electrode is not especially limited, for example, the inner electrode may be made of Ag/AgCl, $Hg/Hg_2Cl_2$, $Hg/Hg_2SO_4$ or the like. Among these, the present claimed invention performs effectively when the inner electrode is the Ag/AgCl electrode, since electric potential fluctuation is caused readily because Ag is oxidized and AgCl becomes silvernegatively charged chloride ion due to the ultraviolet rays (the maximum absorption wavelength 200 nm). The electric potential fluctuation of the Ag/AgCl electrode due to ultraviolet rays is not especially limited as long as the light contains ultraviolet rays. For example, the electric potential fluctuation can be caused by, not only irradiation of light from a fluorescent lamp but also sunlight. Irradiating the Ag/AgCl electrode with sunlight causes about 10~100 mV electric potential fluctuation The ultraviolet absorber or the ultraviolet reflecting agent is not especially limited as long as it contains insulative properties, it can be represented by an organic system pigment such as a quinacridone system pigment such as quinacridone red, quinacridone magenta, and quinacridone violet; a dimethyl quinacridone system pigment; a perylene system pigment such as perylene red, perylene orange, perylene maroon, perylene vermilion, and perylene Bordeaux; a diketo pyrrolo pyrrole system pigment such as diketo pyrrolo pyrrole red, and diketo pyrrolo pyrrole orange; a polyazo condensed pigment such as polyazo red, polyazo yellow, chromo phthal orange, chromo phthal red, and chromo phthal scarlet; a disazo system pigment such as disazo yellow; a monoazo system pigment such as monoazo red, monoazo yellow, and monoazo brown; and an isoindolinone system pigment such as isoindolinone yellow. These organic system pigments do not affect an electromotive force of the ion-sensitive membrane. Since an ultraviolet absorber or an ultraviolet reflecting agent such as, for example, a carbon having electrically conductive properties, causes the electric potential fluctuation, it is not appropriate for this invention.

A dosage of the ultraviolet absorber or the ultraviolet reflecting agent to the base material is preferably a mass ratio of the base material to the ultraviolet absorber or the ultraviolet reflecting agent of 1:3~1:10, and more preferably 1:5~1:7.5. As long as the mass ratio falls within this range, even though the ultraviolet absorber or the ultraviolet reflecting agent is added to the base material, this does not prevent the membrane from being made, and as a result sufficient blocking of the ultraviolet rays can be achieved.

Effect of the Invention

In accordance with this invention having the above arrangement, since the electric potential fluctuation of the inner electrode due to the ultraviolet rays can be restrained, it is possible to conduct the analysis with high accuracy.

BEST MODES OF EMBODYING THE INVENTION

One embodiment of this invention will be explained with reference to drawings.

Figure 1:
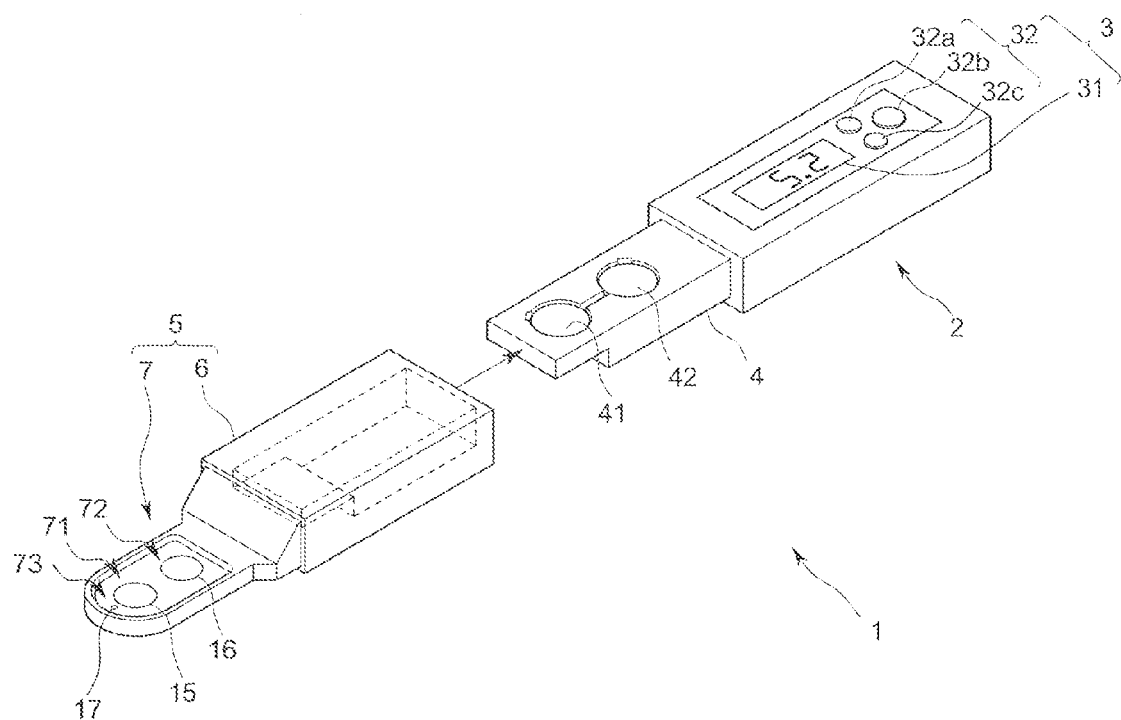
FIG. 1 is an exploded perspective view showing a structure of a liquid membrane type $Na^+/K^+$ electrode in accordance with one embodiment of this invention.
Figure 2:
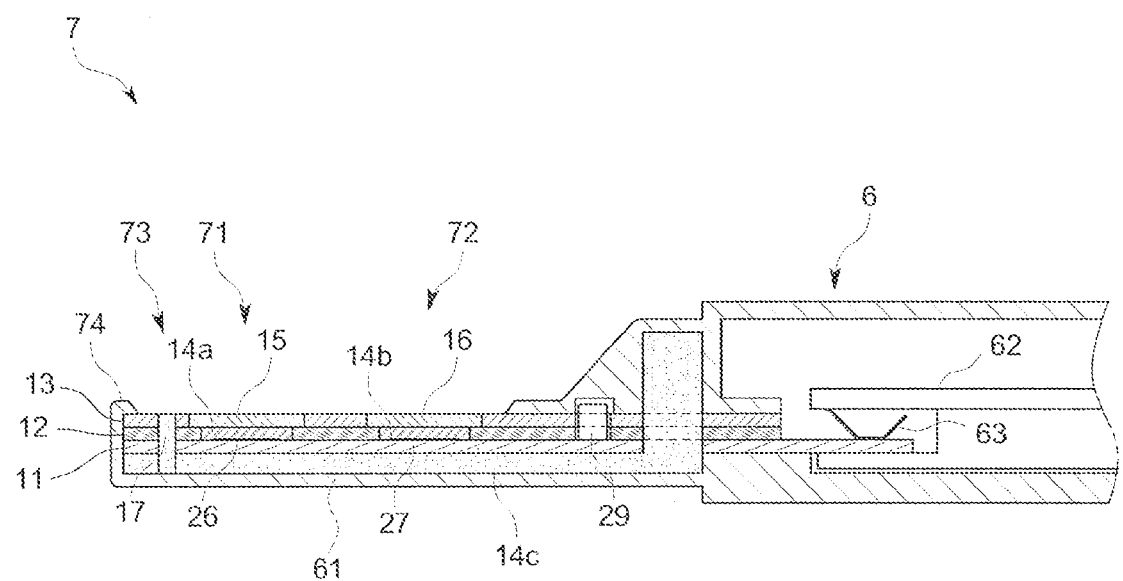
FIG. 2 is a longitudinal cross-sectional view showing a structure of a flat-type sensor of this embodiment.
Figure 3:
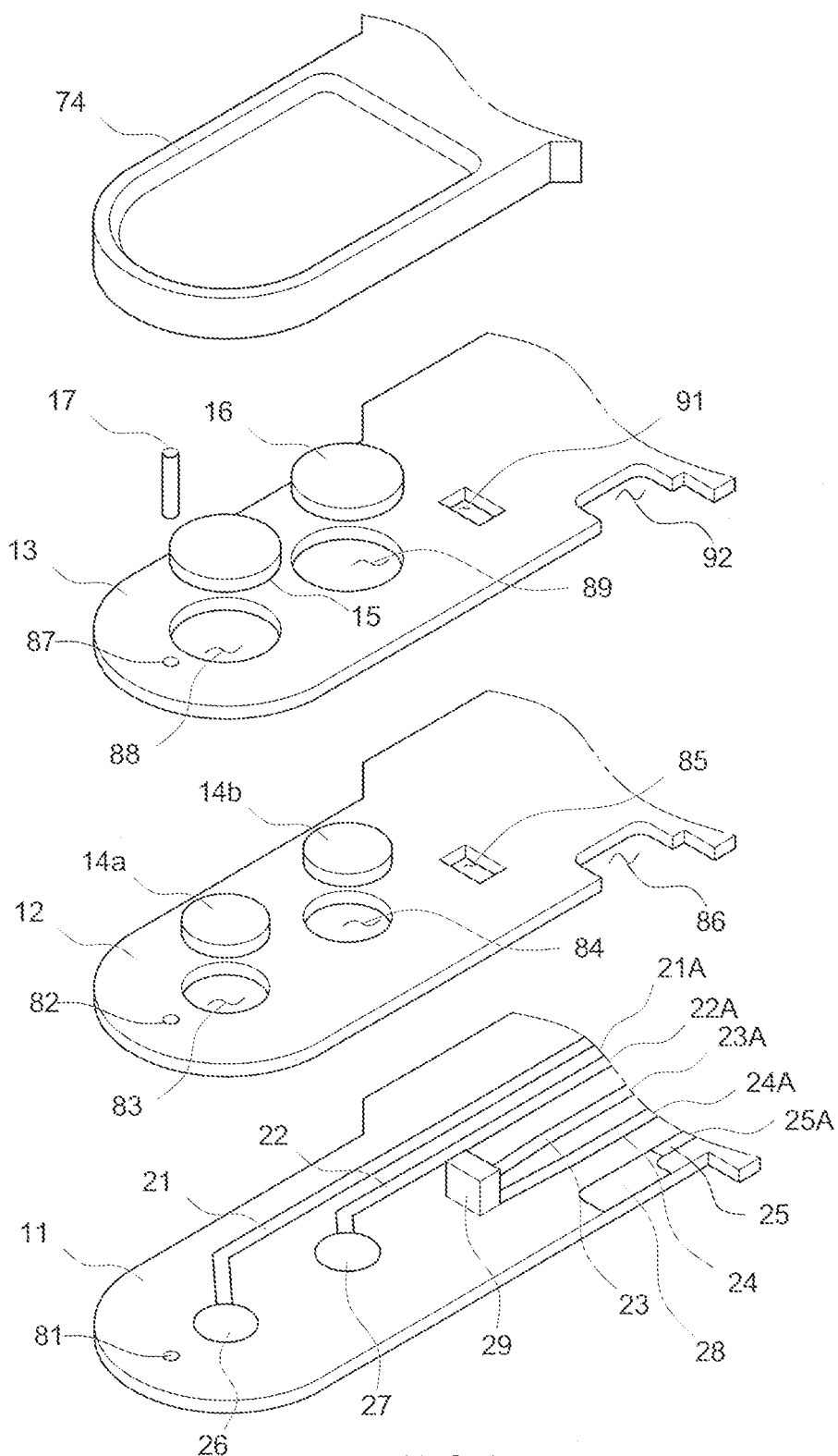
FIG. 3 is an exploded perspective view showing principal parts of the flat-type sensor of this embodiment.

A liquid membrane type $Na^+/K^+$ electrode 1 in accordance with this embodiment is a hybrid type wherein an ion-selective electrode and a reference electrode are integrated for measuring a concentration of a sodium ion and a concentration of a potassium ion in, for example, urine, and as shown in FIG. 1~3, comprises a body 2 made of a resin, an arithmetic processing part (not shown in drawings) such as a micro computer incorporated in the body 2, a display/operation part 3 formed on an upper surface of the body 2, a power source part 4 formed adjacent to the display/operation part 3 and an electrode part 5 made of a synthetic resin and formed in a water-proof structure.

Lead parts 21A, 22A, 23A 24A, and 25A of a flat-type sensor 7, to be described later, and a connecting part 63 that is connected to a circuit substrate 62 having the arithmetic processing part are provided inside of the body 2. The circuit substrate 62 is connected to and supported by a case.

The display/operation part 3 comprises a display part 31 and an operation part 32 that operates various buttons such as a power button 32a, a correction button 32b and a hold button 32c. The power source part 4 comprises button batteries 41, 42.

The electrode part 5 comprises a tubular part 6 whose one end opens to make it possible to house the power source part 4 and a flat-type sensor 7 that is continuously arranged at the other end of the tubular part 6. The electrode part 5 is configured so that it can be integrally connected with the body 2 by being mounted on the body 2 so as to cover the power source part 4 or so that it can be separated from the body 2.

The flat-type sensor 7 is, as shown in FIG. 2 and FIG. 3, made of a material such as polyethylene terephthalate having electrical insulation, and comprises substrates 11, 12, and 13 each of which is laminated. A part of each substrate 11, 12, and 13 is formed in a shape of an arc. The third substrate 13 positioned as the top layer and the second substrate 12 positioned as the middle layer have the same shape (in a plane view), and the arc part of the first substrate 11 positioned as the lower layer is the same as that of the second substrate 12 and the third substrate 13, and other side of the first substrate 11 is longer than that of the second substrate 12 and the third substrate 13. In addition, a detected liquid holder 74 is arranged to surround a peripheral border of the third substrate 13.

Conductive parts 21, 22, 23, 24, and 25 are formed on an upper surface of the first substrate 11 by silk-screen printing, for example, Ag paste after providing a predetermined pretreatment, and a circular through bore 81 is formed on the first substrate 11. The conductive parts 21, 22, 23, 24, and 25 are processed as follows. First, a distal end of the conductive part 21 located at one of the outer sides is covered with AgCl and a circular inner electrode 26 of a $Na^+$ electrode 71 is formed, and a distal end of the conductive part 22 located at an inner side of the conductive part 21 is also covered with AgCl and a circular inner electrode 27 of a $K^+$ electrode 72 is formed. In addition, a distal end of the conductive part 25 located at the other outer side is also covered with AgCl and an inner electrode 28 of a reference electrode 73 having an elongated shape located at one of the side end parts of the substrate 11 is formed. Furthermore, a temperature compensating element 29 such as a thermistor is arranged over a distal end of the conductive part 23 and a distal end of the conductive part 24, wherein the conductive parts 23 and 24 are located at an inner side. The other ends of each conductive part 21, 22, 23, 24, and 25 constitute lead parts 21A, 22A, 23A, 24A, and 25A respectively.

The second substrate 12 is provided with a through bore 82 that is arranged at a position corresponding to the through bore 81 and that has the same diameter as that of the through bore 81 and through bores 83 and 84, each of which is formed at a position corresponding to each of the inner electrode 26 and inner electrode 27 and whose diameters are a little larger than those of the through bores 81 and 82, and a rectangular through bore 85 that is formed at a position corresponding to the temperature compensating element 29 and whose size is generally the same as that of the temperature compensating element 29. Furthermore, an elongated cutout 86 is formed at a side end part corresponding to the inner electrode 28 of the reference electrode 73.

The third substrate 13 is provided with a through bore 87 that is arranged at a position corresponding to the through bores 81 and 82 and that has the same diameter as that of the through bores 81 and 82, through bores 88 and 89, each of which is formed at a position corresponding to each of the through bore 83 and the through bore 84 and whose diameter is a little larger than that of the through bores 83 and 84, and a rectangular through bore 91 that is formed at a position corresponding to the through bore 85 and whose size is generally the same as that of the through bore 85. Furthermore, a cutout 92 whose size is the same as that of the cutout 86 is formed at a position corresponding to the cutout 86.

A liquid junction 17 of the reference electrode 73 composed of a porous body made of polyethylene is inserted into the through bores 81, 82, and 87, each of which is formed at the corresponding position of each of the substrates 11, 12, and 13 respectively. The liquid junction 17 is mounted in a state that the upper surface of the liquid junction 17 is generally flush with an upper surface of the third substrate 13 positioned as the top layer.

A gelled internal solution 14a is mounted on the through bore 83 formed on the second substrate 12 and a gelled internal solution 14b is mounted on the through bore 84 on the second substrate 12. The gelled internal solution 14a is formed into a disk shape and made of a pH buffer solution containing $CaCl_2$ to which a sodium ion is added and to which a gelatinizing agent and a gel evaporation retardant are further added. The gelled internal solution 14b is formed into a disk shape and made of a pH buffer solution containing $CaCl_2$ to which a potassium ion is added and to which a gelatinizing agent and a gel evaporation retardant are further added. A $Cl^-$ concentration of the internal solution is adjusted to 0.1M~the saturated concentration. The gelled internal solution 14a is mounted inside of the through bore 83 in a state that an upper surface of the gelled internal solution 14a projects a little from an upper surface of the second substrate 12, and makes contact with the inner electrode 26 formed on an upper surface of the first substrate 11 through the through bore 83. The gelled internal solution 14b is mounted inside of the through bore 84 in a state that an upper surface of the gelled internal solution 14b projects a little from an upper surface of the second substrate 12, and makes contact with the inner electrode 27 formed on the upper surface of the first substrate 11 through the through bore 84.

A disk shaped sodium ion-sensitive membrane 15 is mounted on the through bore 88 formed on the third substrate 13 and the sodium ion-sensitive membrane 15 makes contact with the gelled internal solution 14a and is fixed to the third substrate 13 in a state that an upper surface of the gelled internal solution 14a is generally flush with the upper surface of the third substrate 13. A disk shaped potassium ion-sensitive membrane 16 is mounted on the through bore 89 formed on the third substrate 13 and the potassium ion-sensitive membrane 16 makes contact with the gelled internal solution 14b and is fixed to the third substrate 13 in a state that the upper surface of the gelled internal solution 14b is generally flush with the upper surface of the third substrate 13. The sodium ion-sensitive membrane 15 faces in close proximity to the inner electrode 26 through the gelled internal solution 14a. The potassium ion-sensitive membrane 16 faces in close proximity to the inner electrode 27 through the gelled internal solution 14b.

The solid sodium ion-sensitive membrane 15 is formed with a procedure of adding a plasticizer, Bis(12-crown-4) as a sodium ionophore, and isoindolinone yellow as an ultraviolet ray absorber to polyvinyl chloride (PVC), dissolving the polyvinyl chloride to which the plasticizer, Bis(12-crown-4) and isoindolinone yellow are added with an organic solvent such as tetrahydrofuran (THF), filling the dissolved polyvinyl chloride into the through bore 88 by means of potting or an ink jet printing method, and heating so as to evaporate the organic solvent.

The potassium ion-sensitive membrane 16 is formed by the same method as that of the sodium ion-sensitive membrane 15 except for using Bis(benzo-15-crown-5) as a potassium ionophore.

A gelled internal solution 14c of the reference electrode 73 is arranged from below the first substrate 11 locating at the lowest layer to the upside of the third substrate 13 locating at the top layer in a case 61 continuously arranged to the tubular part 6. The gelled internal solution 14c is so filled that an upper part and a lower part of the gelled internal solution 14c are in communication through a gap between a side part, in the internal electrode 28 side of the reference electrode 73, of the substrates 11, 12 and 13 and the case 61, and the gelled internal solution 14c makes contact with a surface of the inner electrode 28 of the reference electrode 73 and the lower end part of the liquid junction 17. The gelled internal solution 14c of the reference electrode 73 is an internal solution comprising an $NH_4Cl$ aqueous solution of concentration 0.1M~the saturated concentration to which a gelling agent and a gel evaporation retardant are added.

In accordance with the liquid membrane type $Na^+/K^+$ electrode 1 of this embodiment having the above-mentioned arrangement, even though polyvinyl chloride, having a high permeability to ultraviolet rays, is used as the base material of the liquid membrane type ion-sensitive membranes 15 and 16, since isoindolinone yellow that is mixed with the ion-sensitive membranes 15 and 16 absorbs the ultraviolet rays, it is possible to prevent the ultraviolet rays irradiating the inner electrodes 26 and 27 comprising the Ag/AgCl electrode arranged to face the ion-sensitive membranes 15 and 16 respectively. As a result, it is possible to restrain an electric potential fluctuation of the inner electrodes 26 and 27 due to the ultraviolet rays so that a highly accurate analysis can be conducted.

The present claimed invention is not limited to the above-mentioned embodiment, and a part or all of the above-mentioned embodiment or the modified embodiment can be combined without departing from a spirit of this invention.

EMBODIMENT

The present claimed invention will be explained in further detail with reference to the embodiment, however, this invention is not limited to the embodiment alone.

Five examples of liquid membrane type $Na^+/K^+$ electrode (composite type) of the above-mentioned embodiment of the present claimed invention were manufactured wherein isoindolinone yellow (DA4446 manufactured by Dainichiseika Color & Chemicals Mfg. Co., Ltd.) is mixed with a sodium ion-sensitive membrane and a potassium ion-sensitive membrane, and five comparative examples, whose specification is the same as that of the present claimed invention except that isoindolinone yellow is not mixed with the sodium ion-sensitive membrane and the potassium ion-sensitive membrane, were manufactured.

A drop of $CaCl_2$ aqueous solution containing sodium ions and potassium ions is placed on each ion-sensitive membrane of the obtained liquid membrane type $Na^+/K^+$ electrode and the generated electric voltage under the direct sunlight (61 kLux) in outdoors or in a light shielded state are respectively measured. The results are shown in Table 1 and Table 2. A tolerated value for electric potential fluctuation is 0±3 mV.

TABLE 1

| Comparative Examples | | ΔE (mV) under direct sunlight | ΔE (mV) light shielding | error (mV) |
|---|---|---|---|---|
| 1 | $Na^+$ | −25.4 | −1.2 | −24.2 |
|   | $K^+$  | −1.2  | 16.3 | −17.5 |
| 2 | $Na^+$ | −21.3 | −1.2 | −20.1 |
|   | $K^+$  | −8.5  | 8.3  | −16.8 |
| 3 | $Na^+$ | −1.4  | 12.8 | −14.2 |
|   | $K^+$  | −6.5  | −1.4 | −5.1 |
| 4 | $Na^+$ | −12.6 | −5.8 | −6.8 |
|   | $K^+$  | −12.6 | −6.8 | −5.8 |
| 5 | $Na^+$ | −20.2 | 11.0 | −31.2 |
|   | $K^+$  | −17.0 | −9.0 | −8.0 |
| average | | — | — | −15.0 |
| 3σ | | — | — | 26.1 |
| Cpu | | — | — | 0.7 |
| Cpl | | — | — | 0.5 |

TABLE 2

| Examples | | ΔE (mV) under direct sunlight | ΔE (mV) light shielding | error (mV) |
|---|---|---|---|---|
| 1 | $Na^+$ | −0.6  | −0.6  | 0.0 |
|   | $K^+$  | −9.4  | −9.4  | 0.0 |
| 2 | $Na^+$ | −6.8  | −6.6  | −0.2 |
|   | $K^+$  | −8.6  | −8.6  | 0.0 |
| 3 | $Na^+$ | −19.4 | −19.3 | −0.1 |
|   | $K^+$  | −8.0  | −8.0  | 0.0 |
| 4 | $Na^+$ | −13.4 | −13.4 | 0.0 |
|   | $K^+$  | −16.4 | −16.6 | 0.2 |
| 5 | $Na^+$ | −0.6  | −0.6  | 0.0 |
|   | $K^+$  | −9.4  | −9.4  | 0.0 |
| average | | — | — | 0.0 |
| 3σ | | — | — | 0.3 |
| Cpu | | — | — | 10.1 |
| Cpl | | — | — | 10.0 |

Based on the results shown in Table 1 and Table 2, some of the comparative examples show an influence from the ultraviolet rays of over 20 mV in the negative direction, corresponding to a change equal to or more than twice (corresponding to a change of −18 mV in electric potential) the ion concentration. Correspondingly, the influence from the ultraviolet rays for this invention is within ±0.2 mV, which is sufficiently less than the tolerated value for electric potential fluctuation, and there is no need to consider the influence from the ultraviolet rays when a measurement is conducted. Accordingly, based on this examination it becomes clear that the electric potential fluctuation is effectively restrained by mixing the ultraviolet ray absorbent with the ion-sensitive membrane, thereby enabling a highly accurate analysis to be conducted.

EXPLANATION OF REFERENCE CHARACTERS

1 . . . liquid membrane type $Na^+/K^+$ electrode
14a . . . gelled internal solution $Na^+$ electrode
14b . . . gelled internal solution $K^+$ electrode
15 . . . sodium ion-sensitive membrane
16 . . . potassium ion-sensitive membrane
26 . . . inner electrode of $Na^+$ electrode
27 . . . inner electrode of $K^+$ electrode
71 . . . $Na^+$ electrode
72 . . . $K^+$ electrode

The invention claimed is:

1. A liquid membrane type ion-selective electrode, comprising
    a liquid membrane type ion-sensitive membrane wherein a predetermined ionophore is supported by a base material,
    an inner electrode that has electrical conductivity and is arranged at a position on which light that has transmitted through the ion-sensitive membrane is incident, and
    an internal solution that contains an electrolyte and makes contact with the ion-sensitive membrane and the inner electrode, wherein
    the ion-sensitive membrane contains a mixture of a resin, an ionophore, and a material selected from the group consisting of an ultraviolet absorber or an ultraviolet reflecting agent, both the ultraviolet absorber and the ultraviolet reflecting agent having an insulative property sufficient to restrain an electric potential fluctuation of the inner electrode due to ultraviolet rays without affecting a measurement by the electrode, thereby preserving the ion-sensitivity of the ion-sensitive membrane, the ultraviolet absorber restraining electric potential fluctuation of the inner electrode by absorbing ultraviolet rays and the ultraviolet reflecting agent restraining electric potential fluctuation of the inner electrode by reflecting ultraviolet rays.

2. The liquid membrane type ion-selective electrode described in claim 1, wherein
    the base material of the ion-sensitive membrane is made of a resin.

3. The liquid membrane type ion-selective electrode described in claim 1, wherein
    the inner electrode is an Ag/AgCl electrode.

4. The liquid membrane type ion-selective electrode described in claim 1, wherein
    the insulative ultraviolet absorber or ultraviolet reflecting agent is an organic system pigment.

\* \* \* \* \*